US009277854B2

(12) United States Patent
Jung et al.

(10) Patent No.: US 9,277,854 B2
(45) Date of Patent: Mar. 8, 2016

(54) IMAGE SENSOR FOR CAPSULE ENDOSCOPE ENABLING DUAL MODE OPERATION

(75) Inventors: Han Jung, Daejeon (KR); Byung Hyuk Kim, Daejeon (KR); Yong Woo Lee, Daejeon (KR); Chul Cha, Daejeon (KR); Sang Heun Park, Daejeon (KR); Bong Ki Baek, Sejong-si (KR)

(73) Assignee: I3SYSTEM, INC., Daejeon (KR)

( * ) Notice: Subject to any disclaimer, the term of this patent is extended or adjusted under 35 U.S.C. 154(b) by 692 days.

(21) Appl. No.: 13/641,595

(22) PCT Filed: Apr. 14, 2011

(86) PCT No.: PCT/KR2011/002654
§ 371 (c)(1),
(2), (4) Date: Oct. 16, 2012

(87) PCT Pub. No.: WO2011/136489
PCT Pub. Date: Nov. 3, 2011

(65) Prior Publication Data

US 2013/0035547 A1 Feb. 7, 2013

(30) Foreign Application Priority Data

Apr. 29, 2010 (KR) ........................ 10-2010-0040270

(51) Int. Cl.
*A61B 1/045* (2006.01)
*A61B 1/04* (2006.01)
*A61B 1/00* (2006.01)
*A61B 1/05* (2006.01)

(52) U.S. Cl.
CPC ............. *A61B 1/041* (2013.01); *A61B 1/00036* (2013.01); *A61B 1/00163* (2013.01); *A61B 1/00181* (2013.01); *A61B 1/051* (2013.01)

(58) Field of Classification Search
CPC .................... A61B 1/00036; A61B 1/000163; A61B 1/00181
USPC ........................................................... 348/65
See application file for complete search history.

(56) References Cited

U.S. PATENT DOCUMENTS

| | | | |
|---|---|---|---|
| 7,803,108 | B2 | 9/2010 | Honda |
| 7,998,067 | B2 | 8/2011 | Kimoto et al. |
| 2007/0118017 | A1 | 5/2007 | Honda |
| 2007/0135684 | A1 | 6/2007 | Suzushima et al. |
| 2007/0183672 | A1 | 8/2007 | Kotoda |
| 2007/0185381 | A1 | 8/2007 | Kimoto et al. |
| 2008/0015411 | A1 | 1/2008 | Kimoto et al. |
| 2008/0242926 | A1 | 10/2008 | Nishino |

(Continued)

FOREIGN PATENT DOCUMENTS

| | | | |
|---|---|---|---|
| JP | 63-058567 | A | 3/1988 |
| WO | WO 2007/029820 | A1 | 3/2007 |

(Continued)

*Primary Examiner* — Tat Chio
*Assistant Examiner* — Nguyen Truong
(74) *Attorney, Agent, or Firm* — Rabin & Berdo, P.C.

(57) ABSTRACT

The present invention relates to an image sensor for a capsule endoscope which enables a dual mode operation, and more particularly, to an image sensor for a capsule endoscope wherein two image sensors identically designed and manufactured for photographing the inside of a human body are used and set as a master and a slave, respectively so as to enable a dual mode operation in which two chips are linkage-operated.

9 Claims, 4 Drawing Sheets

(56) References Cited

U.S. PATENT DOCUMENTS

| | | | | |
|---|---|---|---|---|
| 2009/0118585 | A1 | 5/2009 | Honda et al. | |
| 2010/0013914 | A1 | 1/2010 | Bettesh et al. | |
| 2010/0271468 | A1 * | 10/2010 | Wang | 348/77 |

FOREIGN PATENT DOCUMENTS

| | | | |
|---|---|---|---|
| WO | WO 2007/055330 | A1 | 5/2007 |
| WO | WO 2007/072850 | A1 | 6/2007 |

* cited by examiner

| Timer Operation (Step) | B0 | b1 | b2 | b3 | b4 | b5 | b6 | b7 |
|---|---|---|---|---|---|---|---|---|
| Sleep Mode | Off | Off | On | Off | Off | On | Off | On |
| Single/Dual Mode | Dual | Dual | - | Single | Dual | - | Dual | - |
| Frame Rate | 5fps | 20fps | 0 | 3fps | 10fps | 0 | 2fps | 0 |
| Timer Duration | 5mins | 20mins | 1hour | 4hours | 7hours | 10hours | 2hours | - |
| Predicted Aim/Purpose | Test | Throat | Stomach | Small Intestine | Large Intestine | - | Confirmation | - |

IMAGE SENSOR FOR CAPSULE ENDOSCOPE ENABLING DUAL MODE OPERATION

TECHNICAL FIELD

The present invention relates to an image sensor for a capsule endoscope which enables a dual mode operation, and more particularly, to an image sensor for a capsule endoscope wherein two image sensors identically designed and manufactured for photographing the inside of a human body are used and set as a master and a slave, respectively so as to enable a dual mode operation in which two chips are linkage-operated.

BACKGROUND ART

An apparatus and a method for collecting video information among the various medical information of the inside of the human body are widely well-known. Recently, an endoscope of the capsule type has been developed from the general wire endoscope and it is used to diagnose different diseases in the medical field.

In the endoscope of the capsule type, in other words, the capsule endoscope, where the patient swallows it like the tablet, the video data of the digestive organ of the inside of the human body, which is caught through the camera of the endoscope, is transmitted to the external receiving device and it can play the video in the monitor.

The moving speed and the movement of the ingesta are different according to the property of each digestive organ of the human body. Especially, since the moving speed thereof is fast in throat and the large intestine is wide, it is not easy to obtain the video information without missing parts.

In order to solve this problem, a bi-directional photographing capsule endoscope equipped a sensor capable of bilaterally photographing a target object (using two image sensors) has been developed away from an one-way manner (using one image sensor) along with the high-speed photography.

When two image sensors for just taking a photograph at high speed are utilized for the bi-directional photographing capsule endoscope, the power consumption of the capsule endoscope is increased to double. In this case, there is a problem in that the operating time is drastically decreased due to the property of the battery. Also, since the image sensor makes up the majority of the total power consumption of the capsule endoscope, it cannot complete the photography of the target organ just as intended owing to the increasing of the consumable current of the image sensor.

Moreover, there are problems in that tow image sensors (master and slave) should be designed and manufactured or a controller for controlling the operation thereof should be added thereto.

DISCLOSURE

Technical Problem

Accordingly, the present invention has been made to solve the above-mentioned problems occurring in the prior art, and an object of the present invention is to provide an image sensor for a capsule endoscope enabling dual mode operation in that two image sensors serves to alternatively block the operation of the internal circuit for a bi-directional photographing capsule endoscope, so that it can be linkage-operated by the low power.

Another object of the present invention is to provide an image sensor for a capsule endoscope enabling dual mode operation in that a linkage operation and a controlling signal of two image sensors can be minimized and the operation of the image sensors designed and manufactured identically can be programmable, so that it can change the setting of the operation of the master and slave and the working speed of the image sensor for the specific duration.

Further another object of the present invention is to provide an image sensor for a capsule endoscope enabling dual mode operation in that an operation of two image sensors can be programmable, so that only one image sensor is operated for the specific duration or it provides a timer function having the sleep mode means for blocking the power supply of two image sensors.

Technical Solution

In order to accomplish this object, there is provided an image sensor for a capsule endoscope enabling dual mode operation having two lens for photographing an inside of animal bodies including a human body and two image sensors capable of using and setting as a master and a slave identically designed and manufactured comprising: a master image sensor device set and operated as the master of two image sensors; and a slave image sensor device set and operated as the slave of two image sensors.

Advantageous Effects

According to the image sensor for the capsule endoscope enabling dual mode operation, there is an effect in that two image sensors serves to alternatively block the operation of the internal circuit for the bi-directional photographing capsule endoscope, so that it can be operated by the low power, thereby completing the photography of the target organ through the capsule endoscope of the present invention.

Also, the linkage operation and the controlling signal of two image sensors can be minimized and the operation of the image sensors designed and manufactured identically can be programmable, so that it can change the setting of the operation of the master and slave and the working speed of the image sensor for the specific duration, thereby providing the single mode operation, the dual mode operation, and the low power operation mechanism.

Moreover, the operation of two image sensors can be programmable, so that only one image sensor is operated for the specific duration or it provides a timer function having the sleep mode means for blocking the power supply of two image sensors, thereby controlling the photographic speed and the operation thereof without a long-distance controller according to the determined time and the purpose.

BRIEF DESCRIPTION OF THE DRAWINGS

The above and other objects, features and advantages of the present invention will be more apparent from the following detailed description taken in conjunction with the accompanying drawings, in which.

DESCRIPTIONS ON REFERENCE NUMBERS FOR THE MAJOR COMPONENTS IN THE DRAWINGS

Figure 1:
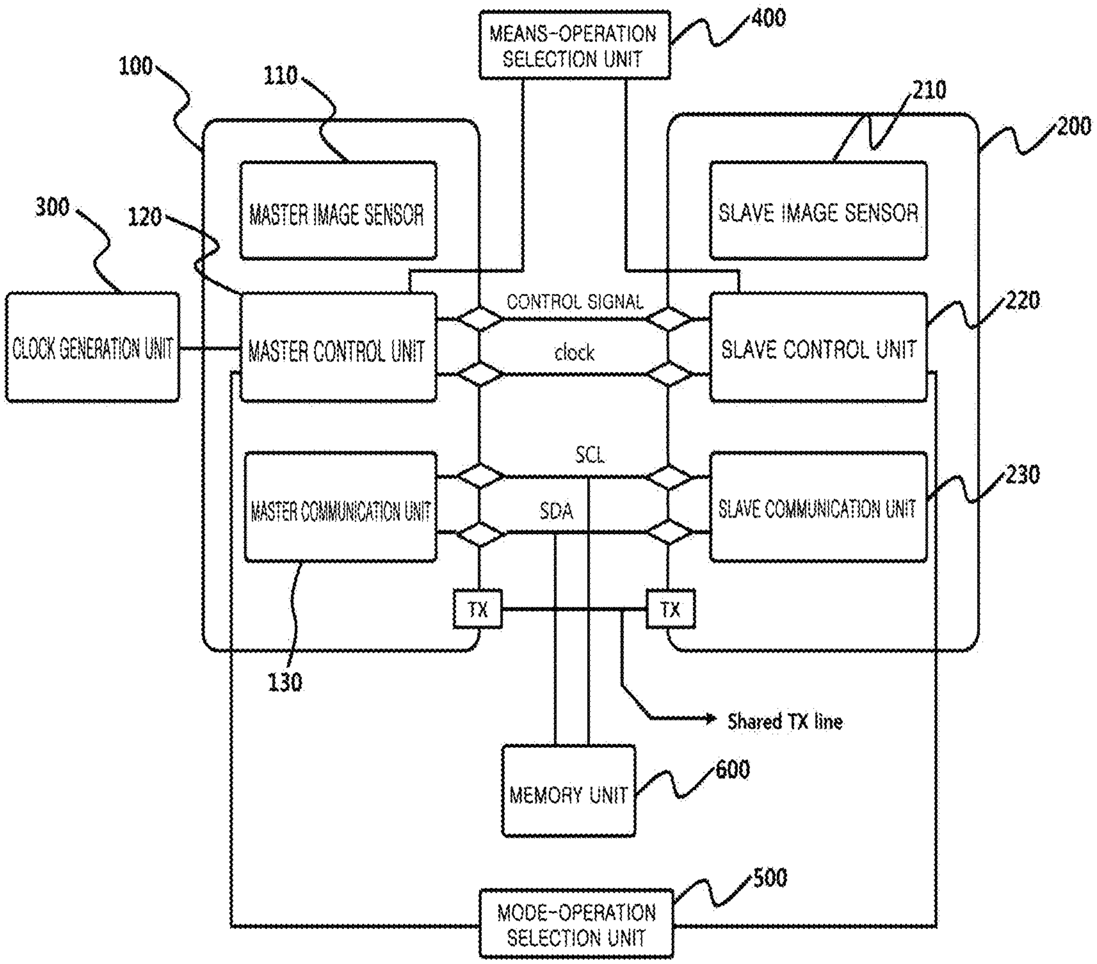
FIG. 1 is a block diagram illustrating an image sensor for a capsule endoscope enabling dual mode operation according to one embodiment of the present invention.

100: master image sensor device
110: master image sensor
120: master control unit
130: master communication unit
200: slave image sensor device
210: slave image sensor
220: slave control unit
230: slave communication unit
300: clock generation unit
400: means-operation selection unit
500: mode-operation selection unit

BEST MODE

Mode for Invention

In order to accomplish these objects, there is provided an image sensor for a capsule endoscope enabling dual mode operation having two lens for photographing an inside of animal bodies including a human body comprising:

a clock generation unit for generating a clock connected to a master image sensor device;

the master image sensor device including a master image sensor for encoding an image which is recorded by one of two lens and outputting an encoded signal thereof, a master control unit for controlling a frame synchronization between the master image sensor and a slave image sensor and an operation of a slave image sensor device, and a master communication unit for communicating with a slave communication unit; and a slave image sensor device including a slave image sensor for encoding an image which is recorded by the other of two lens and outputting an encoded signal thereof, a slave control unit for controlling an operation of the slave image sensor and a slave communication unit according to the control of the master control unit, and the master communication unit for communicating with the master communication unit.

Also, In order to accomplish these objects, there is provided another image sensor for a capsule endoscope enabling dual mode operation having two lens for photographing an inside of animal bodies including a human body comprising:

a clock generation unit for generating a clock connected to a master image sensor device;

the master image sensor device including a master image sensor for encoding an image which is recorded by one of two lens and outputting an encoded signal thereof, a master control unit for controlling a frame synchronization between the master image sensor and a slave image sensor and an operation of a slave image sensor device, and a master communication unit for communicating with a slave communication unit;

a slave image sensor device including a slave image sensor for encoding an image which is recorded by the other of two lens and outputting an encoded signal thereof, a slave control unit for controlling an operation of the slave image sensor and a slave communication unit according to the control of the master control unit, and the master communication unit for communicating with the master communication unit; and an operation selection unit for setting up in order to operate at least one of the master image sensor device and the slave image sensor device.

At this time, the operation selection device 400 comprises a means-operation selection unit for setting up in order to operate any one of the master image sensor device and the slave image sensor device; and a mode-operation selection unit 500 for setting up in order to operate only one of the master image sensor device and the slave image sensor device or operate them at the same time.

Also, the image sensor for the capsule endoscope enabling dual mode operation further comprises a memory unit for storing an information for setting up a detail operation of the image sensor.

Here, a sleep mode by each step, a single/dual mode, a frame rate, and a timer duration information are stored in the memory unit and the image sensor further comprises a timer for counting the elapsed time.

Here, it is connected to the ground (GND) in case of being set up as the master image sensor device and it is connected to the VDD in case of being set up as the slave image sensor device.

Here, the slave image sensor device receives the clock generated from the master image sensor device or shares with the master image sensor device so as to receive the clock.

Here, when it is set up as the single mode in the mode-operation selection unit, an output of the clock and an output of a control signal of the master image sensor device maintain a low state (0), so that a power of the slave image sensor device is not used up.

Here, the master image sensor device controls the operation of the slave image sensor device by using only the control signal and the clock signal, so that it can minimize a power consumption thereof.

In order to accomplish these objects, there is provided further another image sensor for a capsule endoscope enabling dual mode operation having two lens for photographing an inside of animal bodies including a human body comprising:

a clock generation unit for generating a clock connected to a master image sensor device;

the master image sensor device including a master image sensor for encoding an image which is recorded by one of two lens and outputting an encoded signal thereof, a master control unit for controlling a frame synchronization between the master image sensor and a slave image sensor and an operation of a slave image sensor device, and a master communication unit for communicating with a slave communication unit;

a slave image sensor device including a slave image sensor for encoding an image which is recorded by the other of two lens and outputting an encoded signal thereof, a slave control unit for controlling an operation of the slave image sensor and a slave communication unit according to the control of the master control unit, and the master communication unit for communicating with the master communication unit;

an operation selection unit for setting up in order to operate at least one of the master image sensor device and the slave image sensor device;

a memory unit for storing an information including a device ID, an image size, a working speed, an operating current, and a LED brightness; and an image data transmission device for outputting the image data, which is outputted by the master image sensor and the slave image sensor, to a receiving device.

At this time, the image data transmission device adds an information data line to a front of the image frame data and assorts the output of the mast image sensor and the slave image sensor.

Here, the information data includes any information such as a device ID (Device(Sensor) ID), a frame counter, a frame rate, and a LED on time.

In order to accomplish these objects, there is provided further another image sensor for a capsule endoscope enabling dual mode operation having two lens for photographing an inside of animal bodies including a human body and two image sensors capable of using and setting as a master and a slave identically designed and manufactured comprising:

a master image sensor device set and operated as the master of two image sensors; and a slave image sensor device set and operated as the slave of two image sensors.

In order to accomplish this object, there is provided an image sensor for a capsule endoscope enabling dual mode operation comprising:

an operation selection unit for setting up in order to operate at least one of a master image sensor device and a slave image sensor device;

the master image sensor device set and operated as a master according to a setting of the operation selection unit; and a slave image sensor device set and operated as a slave according to the setting of the operation selection unit.

In order to accomplish these objects, there is provided further another image sensor for a capsule endoscope enabling dual mode operation comprising:

an operation selection unit for setting up in order to operate at least one of a master image sensor device and a slave image sensor device;

the master image sensor device set and operated as a master according to a setting of the operation selection unit;

a slave image sensor device set and operated as a slave according to the setting of the operation selection unit; and a memory unit for storing an information for setting up a detail operation of the image sensor device and the slave image sensor device.

At this time, the master image sensor device comprises;

a master image sensor for encoding an image which is recorded by one of two lens and outputting an encoded signal thereof; and a master control unit for controlling a frame synchronization between the master image sensor and a slave image sensor and an operation of a slave image sensor device.

Here, the master image sensor device comprises;

a master image sensor for encoding an image which is recorded by one of two lens and outputting an encoded signal thereof;

a master control unit for controlling a frame synchronization between the master image sensor and a slave image sensor and an operation of a slave image sensor device; and a master communication unit for communicating with a slave communication unit.

Here, the master image sensor device further comprises a master image data transmission unit for outputting the image data, which is outputted by the master image sensor, to a receiving device.

Here, the slave image sensor device comprises;

a slave image sensor for encoding an image which is recorded by the other of two lens and outputting an encoded signal thereof; and a slave control unit for controlling an operation of the slave image sensor and a slave communication unit according to the control of the master image sensor device.

Here, the master image sensor device comprises;

a slave image sensor for encoding an image which is recorded by the other of two lens and outputting an encoded signal thereof;

a slave control unit for controlling an operation of the slave image sensor and a slave communication unit according to the control of the master image sensor device; and a slave communication unit for communicating with a master communication unit.

Here, the slave image sensor device further comprises a slave image data transmission unit for outputting the image data, which is outputted by the slave image sensor, to a receiving device.

Here, the operation selection device 400 comprises a means-operation selection unit for setting up in order to operate any one of the master image sensor device and the slave image sensor device; and a mode-operation selection unit 500 for setting up in order to operate only one of the master image sensor device and the slave image sensor device or operate them at the same time.

Hereinafter, an exemplary embodiment of the present invention will be described in detail with reference to the accompanying drawings.

FIG. 1 is a block diagram illustrating an image sensor for a capsule endoscope enabling dual mode operation according to one embodiment of the present invention.

As shown in FIG. 1, the image sensor for a capsule endoscope enabling dual mode operation according to the present invention includes;

two lens identically designed and manufactured for photographing an inside of animal bodies including a human body;

a clock generation unit 300 for generating a clock connected to a master image sensor device 100;

the master image sensor device 100 including a master image sensor 110 for encoding an image which is recorded by one of two lens and outputting an encoded signal thereof, a master control unit 120 for controlling a frame synchronization between the master image sensor and a slave image sensor and an operation of a slave image sensor device, and a master communication unit 130 for communicating with a slave communication unit;

a slave image sensor device including a slave image sensor for encoding an image which is recorded by the other of two lens and outputting an encoded signal thereof, a slave control unit 220 for controlling an operation of the slave image sensor and a slave communication unit according to the control of the master control unit, and the master communication unit for communicating with the master communication unit; and an operation selection unit (not shown) for setting up in order to operate at least one of the master image sensor device and the slave image sensor device.

At this time, the operation selection device includes a means-operation selection unit 400 for setting up in order to operate any one of the master image sensor device and the slave image sensor device; and a mode-operation selection unit 500 for setting up in order to operate only one of the master image sensor device and the slave image sensor device or operate them at the same time.

A SCL shown in FIG. 1 is the abbreviation of the Serial Clock. Also, a SDA is the abbreviation of the Serial Data. A TX is a modulated Serial Output and means any signal transmitted in the capsule.

That is, the TX means an image data transmission device for outputting the image data, which is outputted by the master image sensor and the slave image sensor, to a receiving device. At this time, the master image sensor is provided with a master image data transmission unit (not shown) and the slave image sensor is provided with a slave image data transmission unit (not shown).

The capsule type endoscope, which can be located in the inside of the body of the general human or the animal, for example, the digestive organ, serves to collect a video information or various information (for example, images of the inside thereof, a PH, a temperature or an electrical impedance etc.) and transmit them to an external receiving device, which is located on the surface of the body, through the body.

To achieve this, the general capsule type endoscope having at two lens serves to acquire the images through the lens and the image sensor, receive the acquired image data through the external receiving device, and output the image data through a signal processing unit.

At this time, in the capsule type endoscope, the shooting speed can be controlled by itself or can be controlled according to the control signal of the signal processing unit, depending on where it is located, in other words, a gullet, a stomach, a small intestine, or a large intestine.

Where the capsule type endoscope 100 is quickly moved in the gullet, it is necessary to take a photograph at high speed. Meanwhile, where the capsule type endoscope 100 is slowly moved in the small intestine, since there are no many movements, it slowly takes a photograph.

Also, the receiving device serves to transmit the received information to the signal processing unit.

At this time, the receiving device can store the signals for a predetermined time.

That is, the receiving device is adhered to the body of the human or the animal, so that the signals received from the capsule type endoscope can be stored for the predetermined time.

Accordingly, as though the human or the animal do not go to the hospital, it can have an endoscope procedure and an endocrine secretion procedure while doing his activity for several hours.

The means-operation selection unit 400 serves to set up in order to operate any one of the master image sensor device and the slave image sensor device.

To achieve this, it is connected to the ground (GND) in case of being set up as the master image sensor device by the means-operation selection unit. In case of being set up as the slave image sensor device, it is connected to the VDD, so that the operation mode of the image sensor means can be set up.

The clock generation unit 300 for generating the clock is connected to the master image sensor device. However, as shown in FIG. 1, it is characterized in that the slave image sensor device receives the clock generated from the master image sensor device or shares with the master image sensor device so as to receive the clock.

In the present invention, the control signal is any signal for controlling the frame synchronization between the master image sensor device and the slave image sensor device and the operation of the slave image sensor device.

Generally, the control signal is performed by an input-output (I/O) pin. At this time, the master image sensor device becomes an output and the slave image sensor device becomes an input.

The SCL/SDA/TX lines shown in FIG. 1 can be shared with the master image sensor device and the slave image sensor device. Where it is shared with the TX line, which is the output of the image sensor devices, since the images should be alternately outputted from the master image sensor device and the slave image sensor device, it is necessary to have the proper time division multiplex.

If it is set up as the single mode in the mode-operation selection unit 500, since the output of the clock of the master image sensor device maintains the low state (0), the power of the digital block of the slave image sensor device is not used up.

Also, since the output of the control signal maintains the low state (0), all analog circuits, which are existed within the slave image sensor device, are shut down, so that the power is not consumed in the slave image sensor device.

The image sensor for the capsule endoscope enabling dual mode operation according to another embodiment of the present invention further includes a memory unit for storing an information for setting up a detail operation of the image sensor.

That is, in connection with the set-up of various resistor information of the image sensor devices according to the dual mode operation, it is programmed in the pad of image sensor devices or the memory unit connected additionally thereto, thereby controlling the detail operation thereof.

If it is necessary to change the option during the operation of the capsule endoscope, the option is set up by using the PDA according the external control. Also, by using the option information in the memory unit, it is read through a register file during the initially booting, so that the image sensor device performs the initial setting thereof.

The resistor information stored in the memory unit may be a device ID, an image size, a working speed, an operating current, a LED brightness etc.

Since the master image sensor device controls the operation of the slave image sensor device by using only the control signal (including the clock signal) and it can minimize the power consumption, the operation of the single mode and dual mode (Master & Slave Operation) and the low power operation mechanism can be achieved through the simple option setting by using two image sensors.

The image sensor devices are operated as the master image sensor device or the slave image sensor device according to the selection of the option. That is, it is operated in the dual mode by using two products, that is, the image sensor devices designed and manufactured identically.

Figure 2:
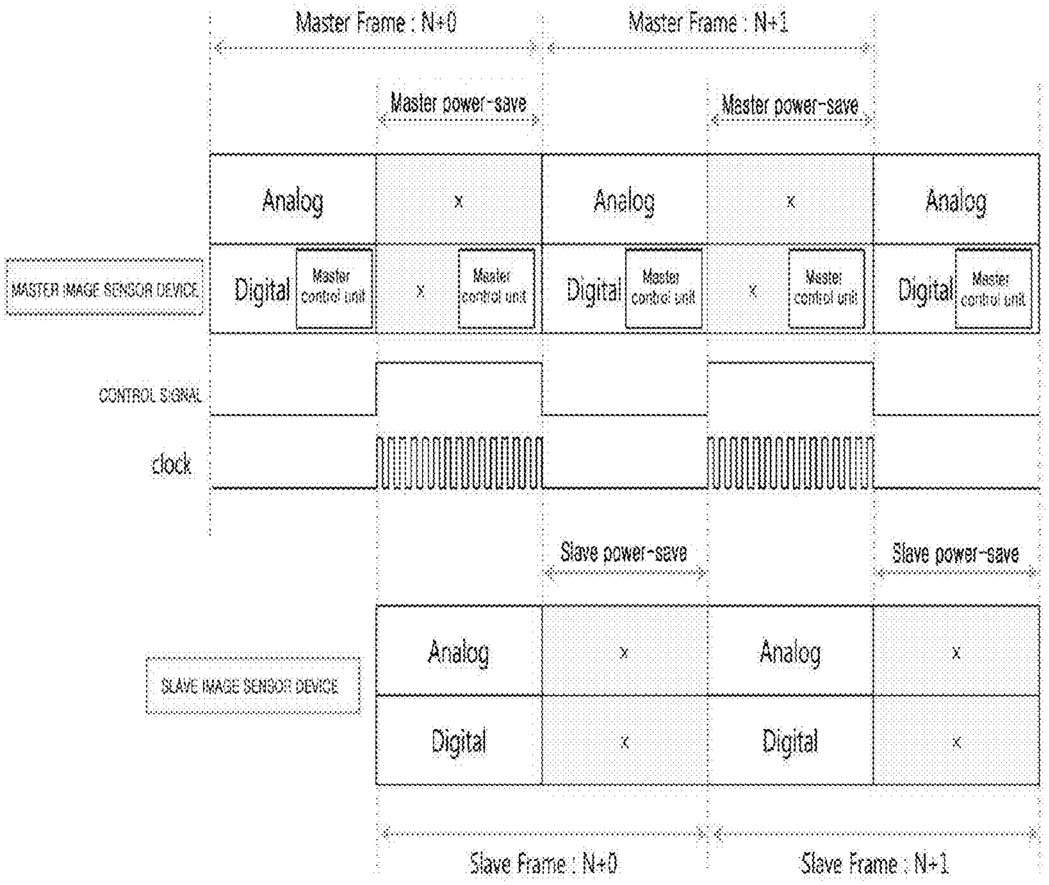
FIG. 2 is an example view illustrating an operation of a dual mode of an image sensor for a capsule endoscope enabling dual mode operation according one embodiment of the present invention.

FIG. 2 is an example view illustrating an operation of a dual mode of an image sensor for a capsule endoscope enabling dual mode operation according one embodiment of the present invention.

As shown, the dual mode, in that the master image sensor device and the slave image sensor device are connected with each other, is alternately operated to a interleave mode.

For example, if each operation of the master image sensor device and the slave image sensor device is 10 fps, the total frame rate becomes 20 fps.

If one image sensor device of the master and slave image sensor devices is operated, other image sensor device becomes a state of a power-down mode (or power-save mode), thereby minimizing the consumption of the electricity.

Where the slave image sensor device becomes the state of the power-save mode, the control signal of the master image sensor device and the output of the clock signal becomes the low state (0), thereby the power consumption of the internal block of the slave image sensor device is not generated.

However, where the master image sensor device becomes the state of the power-save mode, the analog block of the master image sensor device becomes "disabled" and the digital block except for the master control unit becomes "disable.

Where the master image sensor device becomes the power-save mode, it operates only the master control unit, thereby the electrical energy consumption of the master control unit is not nearly generated. Meanwhile, where the slave image sensor device becomes the power-save mode, the power of only the master image sensor is consumed and the power consumption of the slave image sensor device is not generated.

Therefore, two image sensor devices are operated to the dual mode. However, the power consumed at the same time can be minimized, thereby the operating time of the capsule can be improved (it is similar to the use of one image sensor in terms of a consumable current)

The master image sensor device and the slave image sensor device are operated to the power-save mode in the frame thereof. At this time, the power-save mode states are alternately generated, so that the active section, in which the electrical energy consumption is generated, is alternately generated, thereby the power consumption can be minimized.

For your reference, in a case that the power consumption of the silver-oxide battery employed in the capsule endoscope is greatly increased, the operating time thereof is suddenly decreased due to the battery property.

More concretely, in case of the battery capacity of 70 mAh, when the consumable current is 0.1 mA, it is operated for 700 hours. However, when the consumable current is increased up to 100 times as 10 mA, the operating time is drastically decreased, that is, it is operated for less than 7 hours.

The battery employed in the capsule is very small and the silver oxide battery harmless to humans is used. Also, the nominal discharge current is very small.

Figures 3, 4:
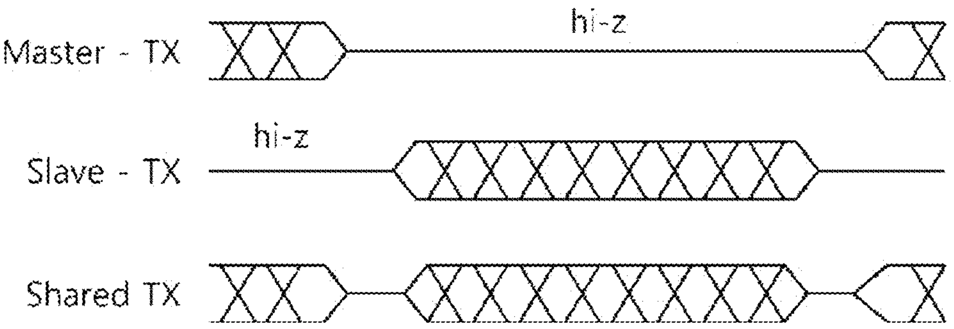
FIG. 3 is an operational flow chart of an image sensor for a capsule endoscope enabling dual mode operation according one embodiment of the present invention.
FIG. 4 is an example view illustrating a programming using a memory unit of an image sensor for a capsule endoscope enabling dual mode operation according one embodiment of the present invention.

FIG. 3 is an operational flow chart of an image sensor for a capsule endoscope enabling dual mode operation according one embodiment of the present invention.

As shown in FIG. 3, in case of the image sensor of a serial output type, the output of two image sensors is shared or the output of the slave image sensor is received in the master image sensor and it fits with a synchronizing signal to be outputted.

FIG. 3 illustrates a case in that the output signals are shared. That is, the timing is intentionally adjusted (time-division multiplexing) in order that the output of the master image sensor and the output of the slave image sensor are not overlapped.

Since the TX PAD of the image sensor, in which the output is not generated, becomes a state of a high impedance, the TX data stream is not defined (it is not effective).

FIG. 4 is an example view illustrating a programming using a memory unit of an image sensor for a capsule endoscope enabling dual mode operation according one embodiment of the present invention.

To achieve this, in the memory unit, a device (sensor) ID, an image size, a working speed, an operating current, a LED information are stored. In addition, a sleep mode by each step, a single/dual mode, a frame rate, a timer duration information are stored.

Moreover, according to another additional aspect of the present invention, the capsule endoscope enabling dual mode operation further includes a timer for operating according to the timer duration stored in the memory unit so as to count the elapsed time.

Meanings of each step indicated in FIG. 4 will be described in detail.

The step B0 is a step for testing an existence of the operation before swallowing the capsule. Two image sensors (the master image sensor and the slave image sensor) have 2.5 fps respectively and are operated for 5 minutes.

The step b1 is a step for photographing at high-speed in the throat after it swallows the capsule. Two image sensors (the master image sensor and the slave image sensor) have 10 fps respectively and are operated for 20 minutes.

The step b2 is a step for taking a picture in the stomach without the movement, the Sleep Mode is operated for 1 hour (Power Saving).

The step b3 is a step for taking a picture in the small intestine moved narrowly and slowly. One image sensor (the master image sensor or the slave image sensor) have 3 fps and is operated for 4 hours.

The step b4 is a step for taking a picture in the wide large intestine having many wrinkles. Two image sensors (the master image sensor and the slave image sensor) have 5 fps respectively and are operated for 7 hours.

The step b5 is a step for the preparation section for confirming No discharging of the capsule. The Sleep Mode is operated for 10 hours (Power Saving).

The step b6 is a step for confirming the discharging state of the capsule. Two image sensors (the master image sensor and the slave image sensor) have 1 fps respectively and are operated for 2 hours. This is a aim of solving the blockage of the capsule.

The image sensor for the capsule endoscope employs the programmable memory unit, so that the option is easily set up in each image sensor during operation of the dual mode and the number of the external PDA is minimized, thereby promoting the convenience of the capsule manufacturing.

Also, for the operation of a timer function, the sleep Mode, the information of the Single/Dual Mode, the Frame Rate, and the Timer Duration etc can be programmable (setting up) in the memory unit by each step, so that the photographic speed and the operation of the capsule endoscope can be controlled according to the region or the purpose (test or confirmation) of the digestive organ.

More concretely, referring to the explanation of the progress step, each step includes the Step 0 (B0) for confirming the existence of the operation before administering through the mouth, the Step 1 (b1) for photographing at high-speed in the throat after it swallows the capsule, the Step 2 (b2) for reducing the power waste of the capsule in the stomach without the movement, the Step (b3) for photographing the small intestine moved narrowly and slowly, the Step 4 (b4) for the wrinkle observation of the large intestine and photographing a case of drastically moving, the Step (b5) for maintaining the dormant state in order to check the blockage and discharging state of the capsule, and the Step 6 (b6) for checking the state of the capsule in order to check the discharge of the capsule or solve the blockage of the capsule. The operating time of the corresponding step can be automatically changed according to the setting of the user.

Figure 5:
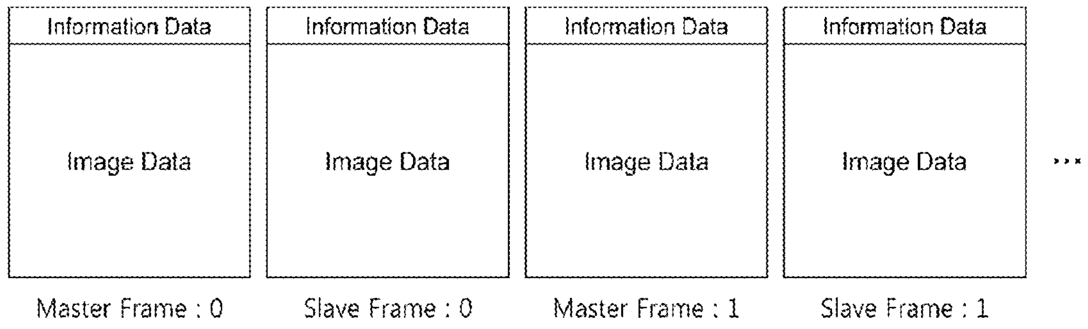
FIG. 5 is an example view illustrating a schematic output data structure of a dual mode operation image sensor for a capsule endoscope enabling dual mode operation according one embodiment of the present invention.

FIG. 5 is an example view illustrating a schematic output data structure of a dual mode operation image sensor for a capsule endoscope enabling dual mode operation according one embodiment of the present invention.

As shown in FIG. 5, it is characterized in that the image data transmission device adds an information data line to a front of the image frame data and assorts the output of the mast image sensor and the slave image sensor. Also, it is characterized in that the information data includes any information such as a device ID (Device(Sensor) ID), a frame counter, a frame rate, and a LED on time.

The LED means any LED formed generally in the capsule so as to clearly photography the image through the image sensor during photographing of the image.

Specifically, in the output of the image sensor, the information data line is added to the front of the image data, thereby assorting the output of the master image sensor and the output of the slave image sensor.

The information data line added to the frame data can include the information the device (Sensor) ID, the frame counter, the frame rate, the LED on time etc. Also, the external receiving device (not shown) serves to search the information data line among the received frame data and assort the received frame data as to whether it is the output of the master image sensor or the output of the slave image sensor not.

Where the many noises are generated, since it is unable to restore the specific frame data to be destroyed, the frame cannot be received in order. Accordingly, the information data line is added, thereby solving the problem in that the specific frame data cannot be restored to be destroyed.

As described above, for the bi-directional photographing capsule endoscope, two image sensors serves to alternatively block the operation of the internal circuit, so that it can be operated by the low power, thereby completing the photography of the target organ through the capsule endoscope of the present invention.

Also, the linkage operation and the controlling signal of two image sensors can be minimized and the operation of the image sensors designed and manufactured identically can be programmable, so that it can change the setting of the operation of the master and slave and the working speed of the image sensor for the specific duration, thereby providing the single mode operation, the dual mode operation, and the low power operation mechanism.

Moreover, the operation of two image sensors can be programmable, so that only one image sensor is operated for the specific duration or it provides a timer function having the sleep mode means for blocking the power supply of two image sensors, thereby controlling the photographic speed and the operation thereof without a long-distance controller according to the determined time and the purpose.

Although a preferred embodiment of the present invention has been described for illustrative purposes, those skilled in the art will appreciate that various modifications, additions and substitutions are possible, without departing from the scope and spirit of the invention as disclosed in the accompanying claims.

INDUSTRIAL APPLICABILITY

The invention relates to an image sensor for a capsule endoscope enabling dual mode operation in that two image sensors serves to alternatively block the operation of the internal circuit for a bi-directional photographing capsule endoscope, so that it can be linkage-operated by the low power, thereby being effectively utilized in the field of the endoscope.

What is claimed is:

1. An image sensor for a capsule endoscope enabling dual mode operation, comprising:

a clock generation unit generating a clock signal;

a master image sensor device including a master image sensor encoding an image acquired through a lens, a master control unit receiving the clock signal from the clock generation unit and outputting the clock signal and a control signal, and a master communication unit for communicating with a slave communication unit; and a slave image sensor device including a slave image sensor encoding an image acquired through a lens, a slave control unit receiving the clock signal and the control signal from the master control unit, and the slave communication unit communicating with the master communication unit; and an operation selection device including a mode-operation selection unit setting the image sensor to work in one of a single mode in which either the master image sensor device or the slave image sensor device is operated, a dual mode in which the master image sensor device and the slave image sensor device are operated in an alternate manner, and a sleep mode in which none of the master image sensor device and the slave image sensor device is operated, and a means-operation selection unit selecting only one of the master image sensor device and the slave image sensor device to work in the single mode when the image sensor is set in the single mode, wherein the master image sensor device, the slave image sensor device, the clock generation unit and the operation selection device are disposed inside a same capsule endoscope, and wherein the master control unit controls, through the clock signal and the control signal, an operation of the slave image sensor device and a frame synchronization between the master image sensor and the slave image sensor.

2. The image sensor for a capsule endoscope enabling dual mode operation as in claim 1, further comprising a memory unit for storing an information for setting up a detail operation of the image sensor.

3. The image sensor for a capsule endoscope enabling dual mode operation as in claim 2, wherein the memory unit stores the sleep mode by each step, the single/dual mode, a frame rate, and a timer duration information and the image sensor further comprises a timer for counting the elapsed time.

4. The image sensor for a capsule endoscope enabling dual mode operation as in claim 1, wherein it is connected to the ground (GND) in case of being set up as the master image sensor device and it is connected to the VDD in case of being set up as the slave image sensor device.

5. The image sensor for a capsule endoscope enabling dual mode operation as in claim 1, wherein the slave image sensor device receives the clock signal outputted from the master image sensor device or shares with the master image sensor device so as to receive the clock.

6. The image sensor for a capsule endoscope enabling dual mode operation as in claim 1, wherein, when it is set up as the single mode in the mode-operation selection unit, an output of the clock and an output of the control signal of the master image sensor device maintain a low state (0), so that a power of the slave image sensor device is not used up.

7. The image sensor for a capsule endoscope enabling dual mode operation as in claim 1 further comprising a memory unit storing an information including a device ID, an image size, a working speed, an operating current, and a LED brightness; and an image data transmission device outputting the image data, which is outputted by the master image sensor and the slave image sensor, to a receiving device.

8. The image sensor for a capsule endoscope enabling dual mode operation as in claim 7, wherein the memory adds an information data line to a front of the image frame data and assorts the output of the mast image sensor and the slave image sensor.

9. The image sensor for a capsule endoscope enabling dual mode operation as in claim 8, wherein the information data includes any information such as a device ID (Device(Sensor) ID), a frame counter, a frame rate, and a LED on time.

* * * * *